(12) United States Patent
Mowlai-Ashtiani

(10) Patent No.: US 11,090,131 B2
(45) Date of Patent: Aug. 17, 2021

(54) SYSTEM AND METHOD FOR TRACKING A SUBJECT

(71) Applicant: Medtronic Xomed, Inc., Jacksonville, FL (US)

(72) Inventor: Ali Mowlai-Ashtiani, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 233 days.

(21) Appl. No.: 15/957,174

(22) Filed: Apr. 19, 2018

(65) Prior Publication Data

US 2019/0321127 A1    Oct. 24, 2019

(51) Int. Cl.
 *A61B 90/00* (2016.01)
 *A61B 46/00* (2016.01)
 *A61B 34/20* (2016.01)

(52) U.S. Cl.
 CPC .............. *A61B 90/39* (2016.02); *A61B 34/20* (2016.02); *A61B 46/00* (2016.02); *A61B 2034/2072* (2016.02); *A61B 2090/3916* (2016.02); *A61B 2090/3983* (2016.02); *A61B 2090/3987* (2016.02); *A61B 2090/3991* (2016.02)

(58) Field of Classification Search
 CPC . A61B 17/8605; A61B 17/861; A61B 17/862; A61B 2090/036; A61B 2090/3916; A61B 2090/3983; A61B 2090/3987; A61B 2090/3991; A61B 17/7074; A61B 17/7076; A61B 17/7077; A61B 17/7079; A61B 17/708; A61B 17/7082; A61B 17/8615; A61B 17/8655; A61B 2017/8655
 See application file for complete search history.

(56) References Cited

U.S. PATENT DOCUMENTS

| 6,203,543 | B1 * | 3/2001 | Glossop | A61B 17/86 606/246 |
| 7,697,972 | B2 | 4/2010 | Verard et al. | |
| RE44,305 | E | 6/2013 | Foley et al. | |
| 8,842,893 | B2 | 9/2014 | Teichman et al. | |
| 2002/0038126 | A1 * | 3/2002 | Dominguez | A61B 90/11 606/130 |
| 2004/0199072 | A1 | 10/2004 | Sprouse et al. | |
| 2005/0216015 | A1 * | 9/2005 | Kreidler | B25B 15/007 606/916 |
| 2008/0161814 | A1 | 7/2008 | McAllister et al. | |
| 2009/0247859 | A1 * | 10/2009 | Daum | A61B 90/10 600/411 |
| 2012/0296171 | A1 * | 11/2012 | Lovell | A61B 17/708 600/213 |
| 2015/0257797 | A1 * | 9/2015 | Biedermann | A61B 17/7082 606/305 |
| 2016/0066958 | A1 * | 3/2016 | Raju | A61B 17/8883 606/270 |

FOREIGN PATENT DOCUMENTS

| CN | 201519139 U | 7/2010 |
| CN | 102727308 A | 10/2012 |
| EP | 1779799 A1 | 5/2007 |

\* cited by examiner

*Primary Examiner* — Martin T Ton
(74) *Attorney, Agent, or Firm* — Harness, Dickey & Pierce, P.L.C.

(57) ABSTRACT

Disclosed is a fixation system and method. The system and method may fix a selected member to a subject during a procedure. The selected member may include a tracking device or registration member.

17 Claims, 5 Drawing Sheets

SYSTEM AND METHOD FOR TRACKING A SUBJECT

FIELD

The subject disclosure relates to a system for tracking a position of a subject, and particularly for connecting a tracking device to a subject.

BACKGROUND

This section provides background information related to the present disclosure which is not necessarily prior art.

A tracking device may be used during a selected procedure to track a position of a selected object to which the tracking device is connected. The tracking device may be tracked with a selected tracking system, such as an optical tracking system that has a line of sight from one or more cameras to the selected tracking device. In positioning the tracking device on an item to be tracked, the tracking device may be used to evaluate the position of the item to which it is attached.

SUMMARY

This section provides a general summary of the disclosure, and is not a comprehensive disclosure of its full scope or all of its features.

A system is disclosed that is able to fix a tracking device to a subject, such as a human subject. It is understood that the tracking device may be fixed to a nonhuman subject or nonliving subject for a selected procedure. The tracking device may be connected in or on a substantially small area at a selected location. In various embodiments, the tracking device may be fixed relative to a scalp or on a scalp of a subject near a location of a procedure, such as an otological, nasal, or similar procedure.

The tracking system may include a central fixation member or holding member and one or more auxiliary or radially positioned members. The radially positioned members may assist in stabilizing the tracking device relative to the central holding member. The assembly, once assembled and connected to the subject, may then be used to track the subject during a procedure.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
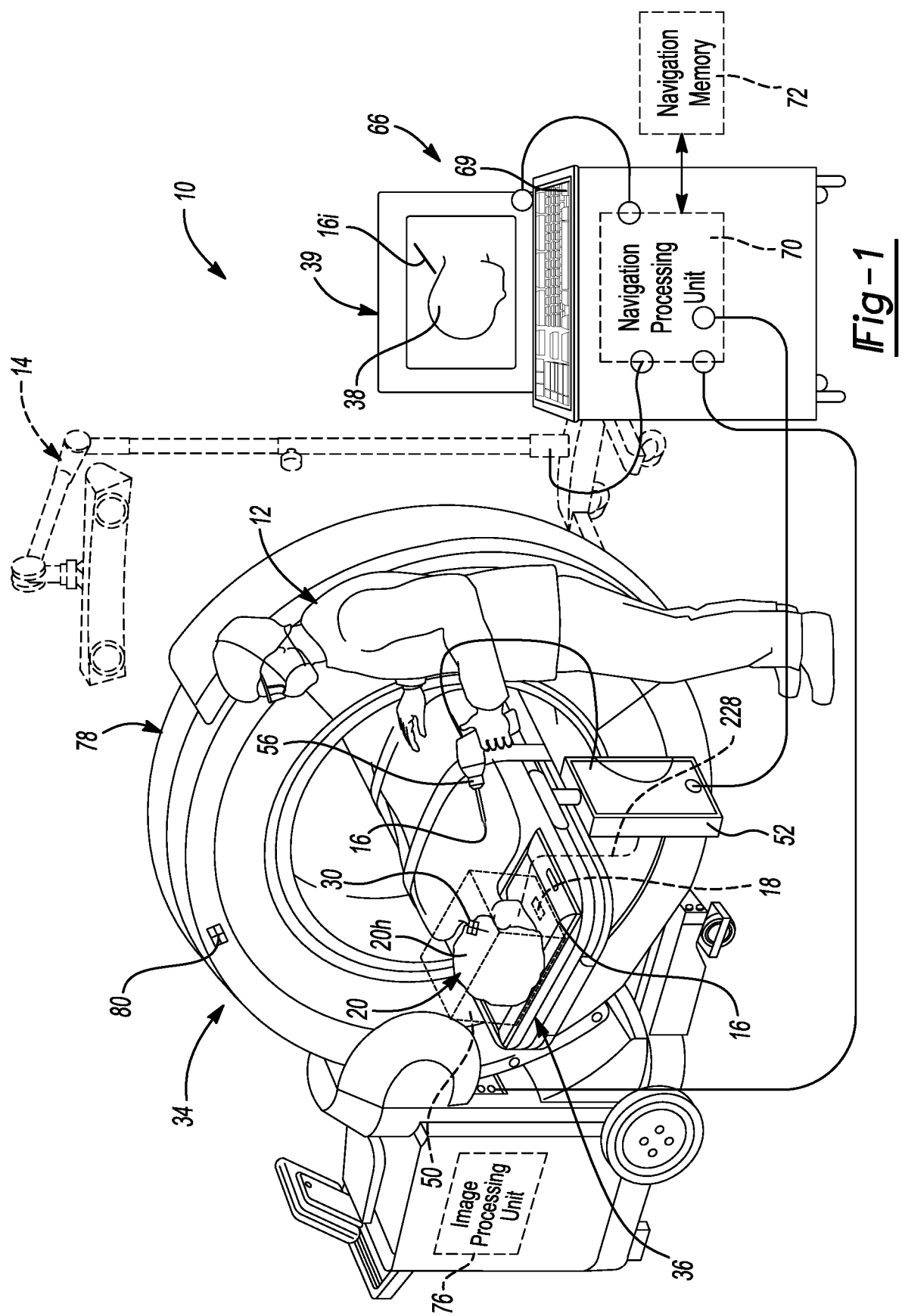
FIG. 1 is a perspective view of a navigation system, according to various embodiments.

With initial reference to FIG. 1, in a procedure a navigation system 10 may be used by a user 12 to perform a selected procedure. The navigation system 10 may include various components that assist in navigating a procedure including a selected tracking system. The tracking system may include various components or portions such as various localizers. Various localizers may include an optical tracking system and/or an electromagnetic tracking system that includes a Tracking Coil Array (TCA) 16. While an optical tracking system may be used with the TCA 16, it is understood that only one tracking system, such as including the TCA 16, may be used with the navigation system 10.

The TCA 16 may include one or more conductive coils 18 positioned relative to a subject 20 on which a procedure is performed. In various embodiments, a procedure may be performed on or near a head 20h of the subject 20. As discussed in further detail herein, a subject tracking device or assembly 30 may be connected to the subject 20, such as to the head 20h of the subject 20. The tracking assembly 30 may also be referred to as a Dynamic Reference Frame (DRF) or a patient tracker.

With continuing reference to FIG. 1, the navigation system 10 may include various features or elements as discussed below. Generally, the navigation system 10 may be used to determine or track a position of an instrument 32 in a volume. The position may include both a three dimensional X,Y,Z location and orientation. Orientation may include one or more degrees of freedom, such as three degrees of freedom. Thus, a total of at least six degrees of freedom may be determined for the position of the instrument 32.

Tracking the position of the instrument 32 may assist the user 12 in determining a position of the instrument 32, even if the instrument 32 is not directly viewable by the user 12. Various procedures may block the view of the user 12, such as performing a repair or assembling an inanimate system, such as a robotic system, assembling portions of an airframe or an automobile, or the like. Various other procedures may include a surgical procedure, such as performing a spinal procedure, neurological procedure, positioning a deep brain simulation probe, or other surgical procedures on a living subject. In various embodiments, for example, the living subject may be a human subject 20 and the procedure may be performed on the human subject 20. It is understood, however, that the instrument 32 may be tracked and/or navigated relative to any subject for any appropriate procedure. Tracking or navigating an instrument for a procedure, such as a surgical procedure, on a human or living subject is merely exemplary.

Nevertheless, in various embodiments, the surgical navigation system 10, as discussed further herein, may incorporate various portions or systems, such as those disclosed in U.S. Pat. Nos. RE44,385; 7,697,972; 8,644,907; and 8,842,893; and U.S. Pat. App. Pub. Nos. 2004/0199072, all incorporated herein by reference. Various components that may be used with or as a component of the surgical navigation system 10 may include an imaging system 34 that is operable to image the subject 20, such as an O-Arm® imaging system, magnetic resonance imaging (MRI) system, computed tomography system, etc. A subject support 36 may be used to support or hold the subject 20 during imaging and/or during a procedure. The same or different supports may be used for different portions of a procedure.

Image data may be acquired during a surgical procedure or acquired prior to a surgical procedure for displaying an image 38 on a display device 39. The instrument 32 may be tracked in a trackable volume or a navigational volume that is produced by a transmitter antenna or transmitting coil array that is incorporated into the localizer 16, as illustrated in FIG. 1. The position of the instrument 32 may be tracked in the tracking volume relative to the subject 20 and then illustrated as an icon 32i with the display device 39. In various embodiments, the icon 32i may be superimposed on the image 38 and/or adjacent to the image 38. As discussed herein, the navigation system 10 may incorporate the display device 39 and operate to render the image 38 from selected image data, display the image 38, determine the position of the instrument 32, determine the position of the icon 32i, etc.

With reference to FIG. 1, the localizer 16 may be an electro-magnetic (EM) localizer that is operable to generate electro-magnetic fields with a transmitting coil array (TCA) 18 which is incorporated into the localizer 40. The TCA 18 may include one or more coil groupings or arrays. In various embodiments, more than one group is included and each of the groupings may include three coils, also referred to as trios or triplets. The coils may be powered to generate or form an electro-magnetic field by driving current through the coils of the coil groupings. As the current is driven through the coils, the electro-magnetic fields generated will extend away from the coils 18 and form a navigation domain or volume 50, such as encompassing all or a portion of a head 20h, spinal vertebrae, or other appropriate portion. The coils 18 may be powered through a TCA controller and/or power supply 52.

The navigation domain or volume 50 generally defines a navigation space or patient space. As is generally understood in the art, the instrument 32, such as a drill, lead, etc., may be tracked in the navigation domain relative to a patient or subject with an instrument tracking device 56. For example, the instrument 32 may be freely moveable, such as by the user 12, relative to the DRF 30 that is fixed relative to the subject 20. Both the tracking devices 30, 56 may include tracking or sensing coils (e.g. conductive material formed or placed in a coil) that senses and are used to measure a magnetic field strength, etc. Due to the tracking device 56 connected or associated with the instrument 32, relative to the DRF 30, the navigation system 10 may be used to determine the position of the instrument 32 relative to the DRF 30.

The navigation volume or patient space may be registered to an image space of the patient and the icon 32i representing the instrument 32 may be illustrated at a navigated (e.g. determined) and tracked position with the display device 39, such as superimposed on the image 38. Registration of the patient space to the image space and determining a position of a tracking device, such as with the tracking device 56, relative to a DRF, such as the DRF 60 may be performed as generally known in the art, including as disclosed in U.S. Pat. Nos. RE44,385; 7,697,972; 8,644,907; and 8,842,893; and U.S. Pat. App. Pub. Nos. 2004/0199072, all incorporated herein by reference.

The navigation system 10 may further include a navigation processor system 66. The navigation processor system 66 may include the display device 32, the localizer 16, the TCA controller 52, and other portions and/or connections thereto. For example, a wire connection may be provided between the TCA controller 52 and a navigation processing unit 70. Further, the navigation processor system 66 may have one or more user control inputs, such as a keyboard 69, and/or have additional inputs such as from communication with one or more memory systems 72, either integrated or via a communication system. The navigation processor system 66, according to various embodiments, may include those disclosed in U.S. Pat. Nos. RE44,385; 7,697,972; 8,644,907; and 8,842,893; and U.S. Pat. App. Pub. Nos. 2004/0199072, all incorporated herein by reference, and/or may also include the commercially available StealthStation® or Fusion™ surgical navigation systems sold by Medtronic Navigation, Inc. having a place of business in Louisville, Colo.

Tracking information, including regarding the magnetic fields sensed with the tracking devices 30, 56, may be delivered via a communication system, such as the TCA controller 52, which also may be a tracking device controller 52, to the navigation processor system 66 including the navigation processor 70. Thus, the tracked position of the instrument 32 may be illustrated as the icon 32i relative to the image 38. Various other memory and processing systems may also be provided with and/or in communication with the processor system 66, including the memory system 72 that is in communication with the navigation processor 70 and/or an imaging processing unit 76. The image processing unit 76 may be incorporated into the imaging system 34, such as the O-Arm® imaging system, as discussed above. The imaging system 34 may, therefore, include various portions such as a source and a x-ray detector that are moveable within a gantry 78. The imaging system 34 may also be tracked with a tracking device 80. It is understood, however, that the imaging system 34 need not be present while tracking the tracking devices, including the instrument tracking device 56. Also, the imaging system 34 may be any appropriate imaging system including a MRI, CT, etc. In various embodiments, the localizer may also include an optical camera system 82. The optical camera system 82 may be used in conjunction with or alternatively to the localizer 16 for tracking the instrument 32.

Information from all of the tracking devices may be communicated to the navigation processor 70 for determining a position of the tracked portions relative to each other and/or for localizing the instrument 32 relative to the image 38. The imaging system 34 may be used to acquire image data to generate or produce the image 38 of the subject 20. It is understood, however, that other appropriate imaging systems may also be used. The TCA controller 52 may be used to operate and power the TCA 40, as discussed above.

With continuing reference to FIG. 1 and additional reference to FIGS. 2A-5, the DRF 30 may be connected to the subject 20 to assist in performing a procedure or tracking a procedure relative to the subject 20. In various embodiments, the DRF 30 may include various components that allow it to be connected relative to the head 20h of the subject 20 to assist in tracking the subject 20, such as the head 20h thereof. The DRF 30, for example, may include an anchor, such as a fixation screw or bolt 100 that is fixable to the head 20h of the subject 20.

The anchor 100 may include a bone engagement portion or region 102 such as including an external thread 104. The external thread 104 may be screwed into the skull of the subject 20 at the head 20h, or other appropriate location. The fixation screw 100 further includes a shaft 108 extending from the threaded or bone fixation portion 102 to a distal or tool engaging region 112. The tool engaging region 112 may include a flange or protuberance, such as a conical region 114. The conical region 114 may be similar to a counter-sink and assist in engaging the soft tissue of the subject 20. The conical region 114 may act as a depth stop or limiter for engaging the anchor 100 into the subject 20 in addition to or alternatively to any depth limiter near the threads 102.

Further the tool engaging region 112 may include a tool or driver connection or engagement 118. In various embodiments, the driver engagement 118 may include a noncircular exterior or facet exterior, such as a hexagonal exterior. The tool engagement region 118 may allow for the anchor 100 to be engaged by a tool 122 to be driven into the head 20h of the subject 20. It is understood, however, that the tool engagement region 118 may be formed in any appropriate configuration to be engaged by the selected tool 122. For example, the tool engaging region 118 may include an internal portion to be engaged by the tool 122.

The tool 122 may include a recess or depression 124 to engage or receive at least a portion of the screw 100. The recess 124 allows the tool 122 to engage the tool engaging region 118. The recess 124 may include an internal wall 126 that has a complementary shape or configuration to engage the tool engaging region 118 of the screw 100. Accordingly, the tool 122 may allow the user 12 to drive the screw 100 into the head 20h of the subject 20.

The screw 100 may further include a base or tracking device engagement region or portion 130. The base engaging region 130 may include a selected configuration such as a protuberance portion 132. The protuberance may be generally spherical or partially spherical in shape. The protuberance 132 may have a diameter or cross section distance 134 (e.g. diameter) greater than a cross sectional dimension 136 of an adjacent region or connection portion 138. Thus, the protuberance 132 may extend out from the connection portion 138. The shaft 108 may further have the diameter or cross-section 109 that is greater than the connection region dimension 136. As discussed herein, therefore, the base or frame assembly 144 may engage the base engagement portion 130, including the base interfering or engagement portion 132 to assist in holding the base or frame assembly 144 relative to the head 20h.

The DRF 30 includes the frame assembly 144 that includes a base or stabilization member or region 160. The stabilization member 160 may be formed as one single member or as more than one member connected together. For example, the stabilization member 160 may be formed as two halves (e.g. two members molded separately) that are then fixed together with selected bolts or pins 162. It is understood, however, that the stabilization member 160 need not be formed as two pieces or more than two pieces, but may be formed as a single piece.

The stabilization portion or member 166 may include a various or selected number of legs or arms, such as a first arm 166, a second arm 168, and a third arm 170. Each of the three arms 166-170 may be positioned at a distance spaced radially from a central portion or hub region 172. In various embodiments, the central portion 172 may surround an axis 173. The axis 173 may be a central axis of the central portion 172 and may be aligned and/or extend from a central axis of the anchor 100. For example, each of the legs 166, 168, and 170 may be positioned at about 120 degrees about or around the central axis 173. It is understood, however, that more than three legs or arms may be provided or that the stabilization portion 160 is formed as a single continuous edge or region that may engage the head 20h. Further, each of the legs 166-170 may extend or have a portion that extends generally parallel with the axis 173. In various embodiments, the legs 166-170 may include a first portion that is connected to the center 172 and extends perpendicular to the axis 173 and a second portion that extends from the first portion generally parallel to the axis 173.

Figure 2A:
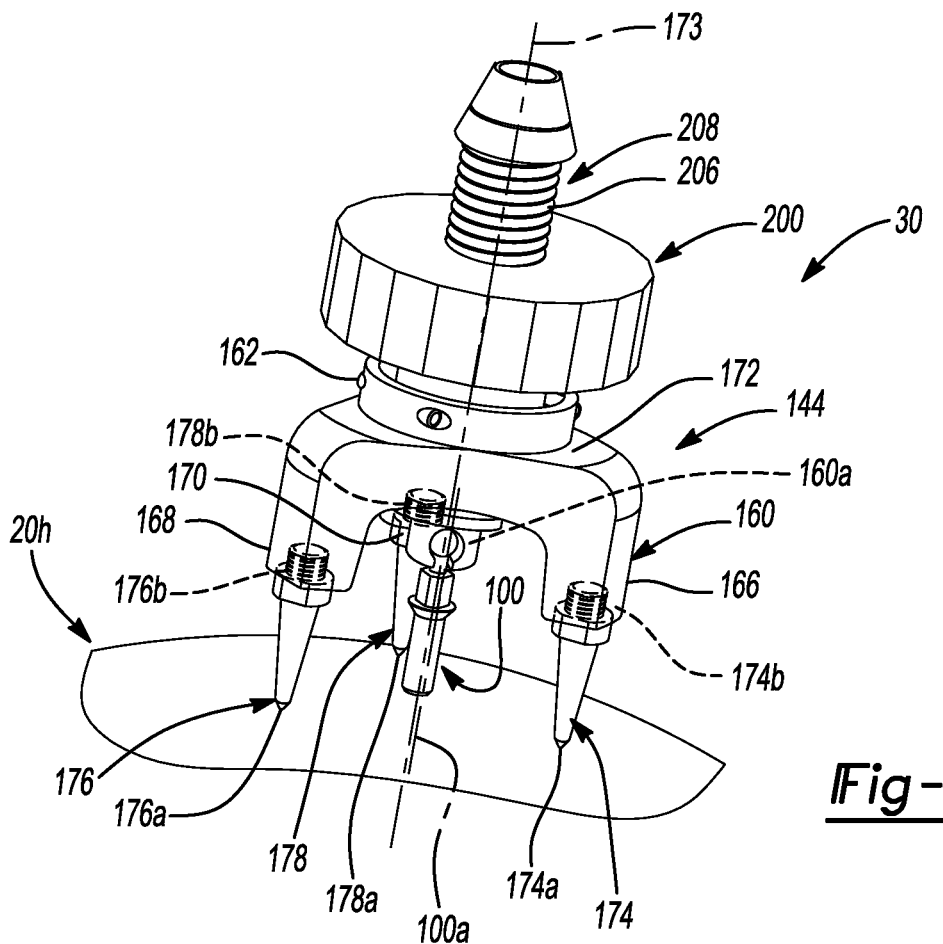
FIG. 2A is a perspective view of a tracking assembly.
Figure 2B:
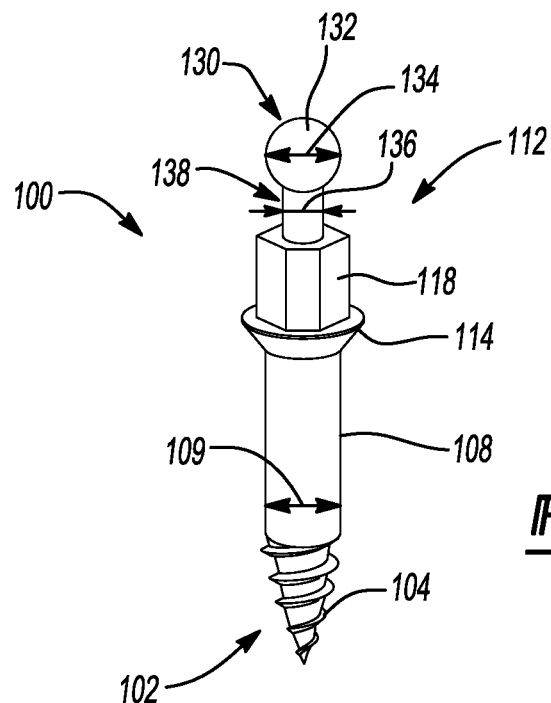
FIG. 2B is a detailed view of an anchor, according to various embodiments.

In various embodiments, as illustrated in FIG. 2A, each of the legs 166-170 includes a scalp engagement projection or member including a first projection 174, a second projection 176, and a third projection 178. Each of the three projections 174-178 may be formed or provided as individual members. Each projection member 174-178 may include portions such as a distal tip which may include a sharp or penetrating region 174a-178a (e.g. about 0.1 mm to about 1 mm in length) and an arm engaging region, such as a externally threaded portion 174b-178b. Accordingly, it is understood that the projections 174-178 may be provided as separate members, such as those including externally threaded portions that are engaged into the respective arms 166-170. It is understood, however, that the projections 174-178 may otherwise be formed such as being molded into the arms 166-170, press fit into the arms 166-170, or other appropriate fixation. Further the projections 174-178 may be formed integrally and as one member with each of the respective arms 166-170. Further, it is understood, that the stabilization portion 160 may be formed as a continuous member (e.g. a cylinder) rather than including separate and spaced apart arms 166-170.

In various embodiments, the stabilization portion 160 may be formed of a selected polymer, such as a substantially ridged polymer. The projections 174-178 may be formed of a selected hard material, such as a metal (e.g. stainless steel, titanium, etc.) that are fitted into the respective arms 166-170. It is further understood, however, that the stabilization portion 160 may be formed as a unitary or single member, such as formed of a selected ridged material (e.g. a metal) where all of the portions are milled from the single piece block. For example, a single piece of stainless steel may be milled to include the stabilization portion 160 including each of the arms 166-170 and projection portions 174-178 having the features as discussed above.

The DRF 30 further includes a central passage through the center 172 to allow a tracking portion or member, such as an elongated member, 182 to pass through the passage. The tracking portion 182 may include or be an elongated member that extends into a portion of the stabilization base 160 to be fixed therein and/or connected thereto. In addition, or alternatively thereto, the tracking portion 182 may extend to an anchor or screw engaging portion or region 188.

The screw engaging region 188 includes a side opening or bore 190 that is complementary to a shape to the anchor engaging portion 130 of the anchor 100. The anchor engaging portion 188 may further include a taper or engagement portion 194 that has a diameter smaller than the diameter 134 of the anchor portion 130 such as complementary to the diameter or cross dimension 136 of the tapered or connection portion 138. Further, a bore or passage may be formed through an end of the anchor engaging region 188. Therefore, the anchor engaging region 188 may be moved over and/or around the ball 132 to engage or hold the ball 132 passed through the opening 190 in the anchor engaging portion 188. The tapered portion 194 may then engage a surface of the ball 130 by passing through or over the tapered region 138 of the anchor 100. An installation of the device 30 as discussed further herein, the brief discussion here illustrates an engagement of the stabilization base 160 to the anchor 100.

In various embodiments, the anchor 100 may otherwise engage the tracking portion 182. For example, the anchor 100 may include a thread (e.g. an external thread) and the tracking portion 182 includes an internal thread. The anchor 100 and the tracking portion 182 may, therefore, be threadably engaged together. Further, the anchor 100 and the tracking portion 182 may be formed as one piece or member. For example, the tracking portion 182 may include an end that is formed as the bone engaging portion 102. In various embodiment, the tracking portion 182 may taper or have a dimension at a selected end similar or identical to those of the anchor discussed above. Thus, the tracking portion 182 may not need the anchor 100 as a separate member and the tracking portion 182 may be the only portion to have the bone engaging portion 102 to engage the subject 20.

The DRF 30 further includes a rotatable knob or nut 200 that includes an internal thread 204 that engages an external thread 206 on a shaft 208 of the tracking portion 182. The knob 200 may include an abutment surface 210 that is configured to engage at the center 172 of the stabilization base 160. By rotating the knob 200 in a selected direction, such as a clockwise direction, the knob 200 may move along the shaft 208 generally in the direction of arrow 212 along the axis 173. The surface 210 of the knob 200 will abut or engage the center 172 of the stabilization portion 160 causing the stabilization portion 160 to move along the shaft 208. As discussed further herein, if the anchor engagement portion 188 is engaging the anchor 100 movement of the knob 200 will cause the stabilization base 160 to move along the axis 173 in the direction of arrow 212 toward a surface or scalp of the head 200h.

Figure 5:
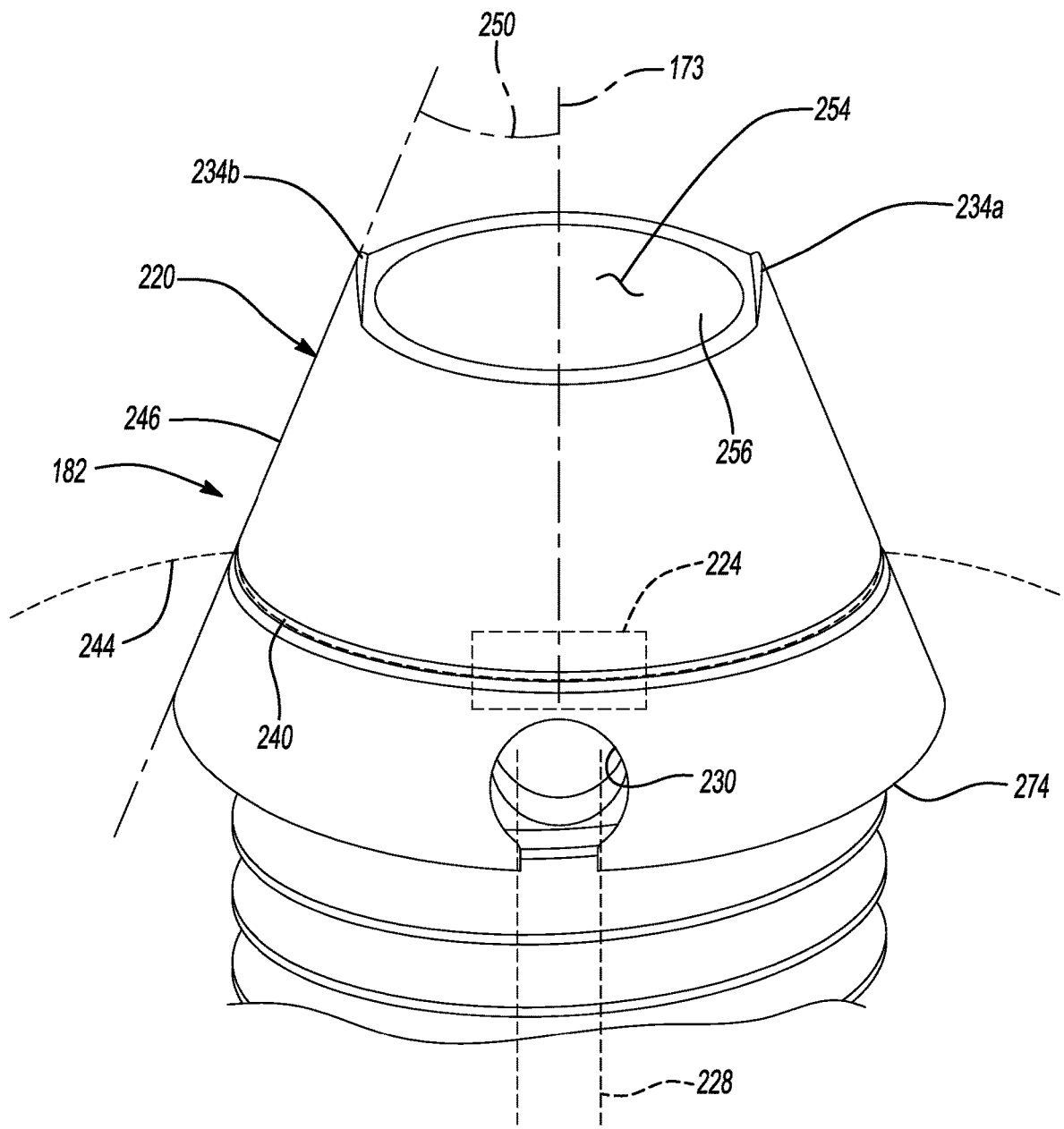
FIG. 5 is a detailed view of a distal portion of the reference assembly.

With continuing reference to FIG. 2A and additional reference to FIG. 5 the tracking portion 182 includes a distal end 220. The distal end 220 may include various features or elements, such as a tracking device 224. The tracking device 224 may be fit within the distal end 220. In various embodiments, the tracking device 224 may be placed in a portion, such as a distal hollowed or empty end, of the shaft 208. The tracking device 224 may include one or more coils that are configured to sense a field generated in the navigation volume 50, as illustrated in FIG. 1. The field may be sensed by the tracking device 224 as discussed above. Accordingly, a position of the tracking device 224 may be determined relative to other tracking device, such as the tracking device 56 on the instrument relative to the instrument 16.

The tracking device 224 may be formed with the distal portion 220, such as molding the tracking portion 182 as a member and molding therein the tracking device 224. Alternatively, the tracking portion 182 may be formed as separate pieces and the tracking device 224 may be positioned within the distal region 220. Further, the tracking device 224 may communicate within the navigation system 10 wirelessly, such as wirelessly transmitting a signal, or transmitting a signal over a wire, such as a wire communication 228. It is understood, however, that the wire communication 228 may represent both the wired or wireless communication. Nevertheless, the distal portion 220 may include a bore or passage 230 to allow passage of the wire 228.

The distal portion 220 may further include a distal or terminal projection or point 234. In various embodiments, the distal portion 220 may include a first point 234a and a second point or projection 234b. The projections 234 may be used to cut a selected material, such as a surgical drape 244. Further, the distal portion 220 may include a groove or catch portion 240 that may assist in holding or capturing a portion of the drape 244 (illustrated in FIG. 5) in the groove 240. It is understood that the capture region may include the groove 240 and/or include a protuberance or ledge to assist in capturing the drape 244.

Accordingly, as discussed further herein, a surgical drape may be moved over or past, such as by being pressed over, the projections 234 and slid down an exterior wall 246 (which may be tapered and conical) of the distal portion 220 to engage the groove 240 or other appropriate drape capture portion. The external wall 246 may be substantially smooth and selectively tapered, at an angle 250 relative to the central axis 173. In various embodiments, the angle 250 may be about 10 degrees to about 50 degrees, including about 10 degrees to about 40 degrees, further including about 18 degrees to about 22 degrees. The distal portion 220 may, therefore, generally form or define a truncated cone. Also, the distal portion 220 may be formed as a single portion or member with the shaft 208 or formed separately and connected to the shaft 208. The distal portion 220 may form a stop or limiter to movement of the knob 200.

Further the distal portion 220 may include a recess or depression 254 having a wall 256. The depression 254 may be a registration depression or divot. In use, as discussed above, the DRF 30 may be registered to the patient by tracking an instrument relative to the divot 254. Further other instruments may be calibrated or registered relative to the DRF 30 by positioning a selected portion of the instrument, such as distal tip of the instrument 16, in the divot 254. The depression 254 may allow instruments to be registered or calibrated relative to the DRF 30 during a selected procedure.

Figure 3:
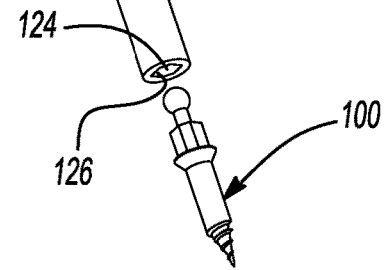
FIG. 3 is a tool for insertion of the anchor.
Figure 6:
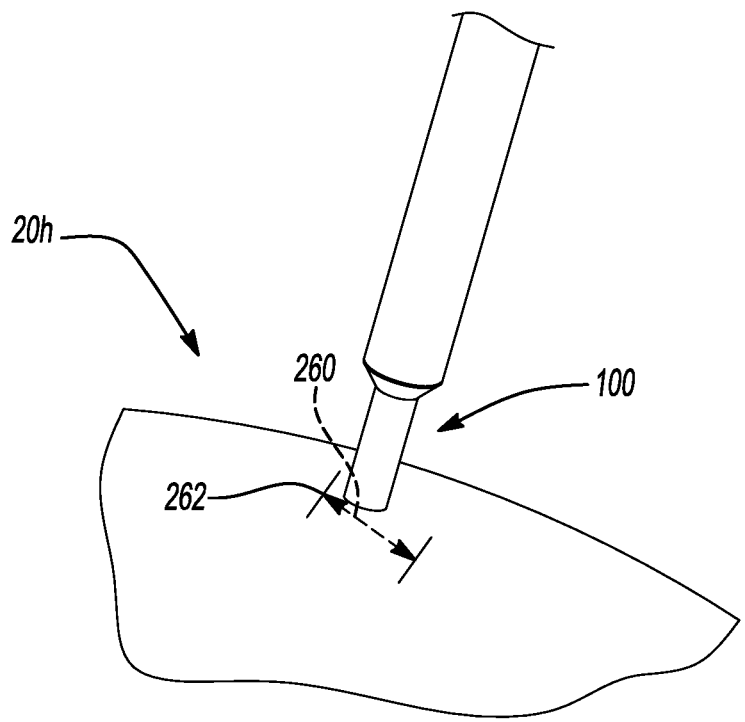
FIG. 6 is a detail environmental view of positioning an anchor.
Figure 7:
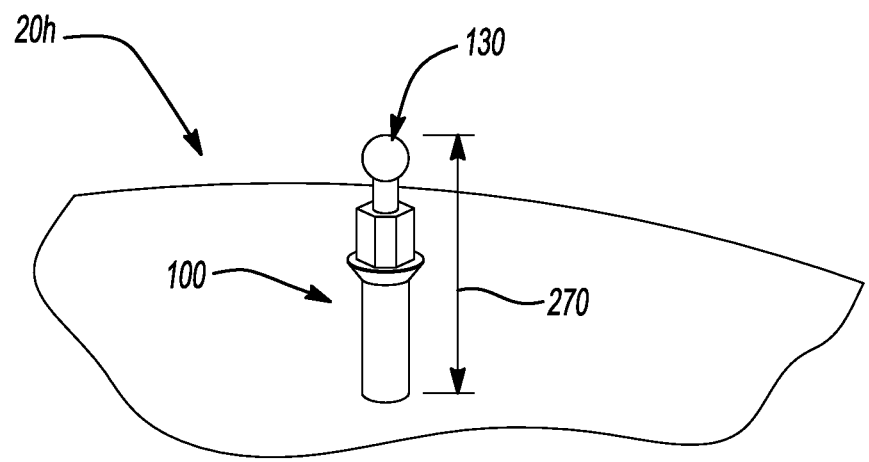
FIG. 7 is a detail prospective view of an anchor positioned in a subject.

With continuing reference to FIGS. 1-5 and additional reference to FIGS. 6 and 7, a process for connecting the DRF 30 to the subject 20 is described and illustrated. As discussed above, the tool 122 may be used to engage the anchor 100 as illustrated in FIG. 3. The anchor 100 may be positioned into a portion of the skull having a selected bone thickness. In various embodiments, an appropriate or a selected bone thickness may be about 3 millimeters (mm) to about 10 mm, or greater; further including about 3 mm to about 6 mm, and further including about 5 mm.

To gain access to the skull bone, an incision 260 may be made through a skin layer of the subject 20 in the head at a selected appropriate location. The incision 260 may have a dimension or length of less than about 10 mm, including less than about 5 mm, including less than about 3 mm, and further including about 3 mm. The incision may also be referred to as a stab wound or puncture. Further, the incision 260, in various embodiments may not be required for selected purposes. The anchor 100, or at least the bone engaging portion 102, may be passed through the incision 260 into the bone below the tissue. The tissue, such as the skin of the subject 20, need not be retracted as the bone engagement portion 102 is tapered and the thread 104 may engage the bone below the tissue. A cross section dimension, such as a diameter of the anchor 100 may include the cross sectional dimension 109 that is less than the incision length. For example, the cross sectional dimension 109 of the anchor 100, such as the shaft 108, may be less than about 3 mm, including less than about 2.5 mm, and may be about 2 to about 2.3 mm in diameter. Accordingly, the anchor 100 may be passed through a selectively sized incision, such as one that is about 3 mm in length or less, such as less than 3 mm in length. In various procedures, a 3 mm incision may not require any suturing after a procedure is completed to ensure appropriate or selected healing of the subject 20.

With reference to FIG. 7, the anchor 100 may extend a selected distance above the surrounding tissue such that the base engaging portion 130 is about 1 centimeters (cm) to about 5 cm, including a distance 270, above the surface of the surrounding tissue on the head 20h of the subject 20. In this way the anchor 100 is fixed to the head 20h of the subject 20 and is prepared to receive the stabilization base 160 and the associated tracking portion 182.

Figure 4:
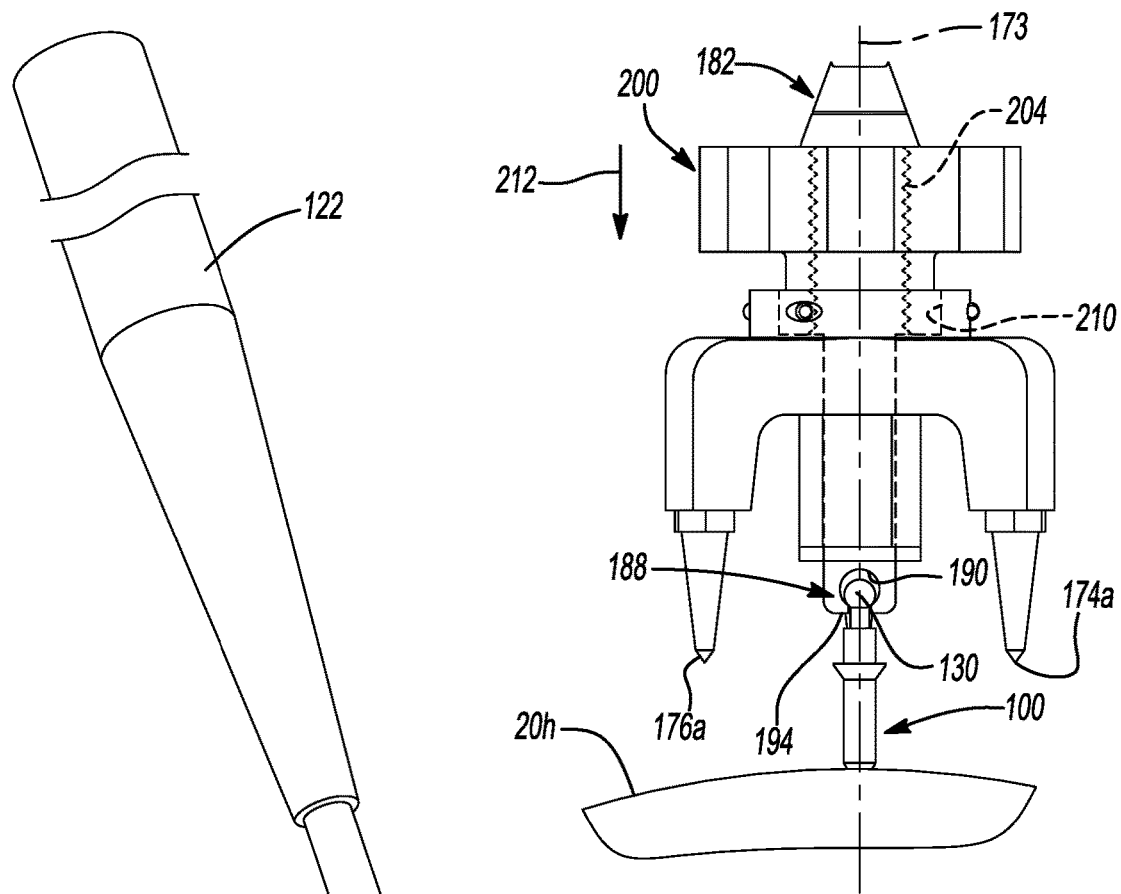
FIG. 4 is a perspective view of the tool assembly in an unanchored position.

With continuing reference to FIG. 7 and additional reference to FIG. 4, the engagement region 188 may be extended a maximum distance relative to the central portion 172 of the base 160. In various embodiments, the knob 200 may be bottomed out on a bottom surface or projection 274 (illustrated in FIG. 5) of the distal portion 220. Accordingly, the anchor engaging region 188 is spaced a furthest distance from the center 172 and the distal tips 174a-178a are spaced a maximum distance from the head 20h.

As illustrated in FIG. 4, the base engaging portion 130 may be passed through the opening 190 into the engaging region 188. After engaging or capturing the base engaging portion 130 in the anchoring engaging portion 188, the knob 200 may be rotated to engage and move the stabilization base 160 toward the head 20h generally in the direction of the arrow 212. After a selected amount of rotation of the knob 200, the stabilization base 160 is moved toward and is configured and does engage the head 20h in a selected manner as illustrated in FIG. 2A.

The base 160 may engage the head 20h to a selected degree. For example, the projections 174-178 may be pushed into a scalp of the subject 20 a selected amount. In various embodiments, the distal points 174a-178a may pierce the external skin of the subject, but not push through the bone surface of the head 20h. It is understood, however, that the projections 174-178 may extend through the tissue of the subject and engage the bone of the head 20h. However the projections 174-176 generally have a diameter, even a maximum diameter, less than that of the anchor 100 (i.e. diameter 109). Accordingly, even if the projections 174-178 pierce the skin of the subject 20, sutures or additional closing techniques may not be required following a procedure.

Once the stabilization base 160 is engaging the head 20h, the DRF 30 is stabilized relative to the head 20h. The stabilization base 160, therefore, is generally three-dimensionally locked or stabilized relative to the head 20h. Further, the combination of the stabilization base engaging the head 20h due to movement along the portion 182 that engages the spherical engaging portion 130 may allow stabilization of the base 160 even if the base is not aligned and/or moving directly along an axis 100a of the anchor 100. Thus, the base have engage and be stabilized relative to the head 20h when it is at an angle 160a relative to the axis 100a of the anchor 100. It is understood, however, that the engaging region 130 of the anchor 100 and the engaging region 188 may be keyed such that a single or one orientation is achieved between the two during stabilization of the base 160.

Regardless, the engagement of the base 160 allows the tracking device 224 in the tracking portion 182 to be used to track a position of the head 20h. The tracking device 224 may be registered to image data, such as the image 38 displayed on the display device 39 (see FIG. 1). Tracking the instrument 32 relative to the DRF 30 may then be possible once both are tracked with the tracking system and the procedure may be navigated with the navigation system, as discussed above.

Further, after the base 160 is engaged to the head 20h to stabilize the DRF 30, the surgical drape 244 may be easily and/or efficiently placed over a portion of the DRF 30. For example, prior to registration the drape 244 may be pushed over the projections 234, as illustrated in FIG. 5. The drape 244 may be pushed over the projections 234 and a small cut may be formed in the drape 244. The drape 244 may generally be formed of an elastic or slightly elastic material which may be passed over the exterior conical surface 246 of the distal end 220 and rebound or be biased to engage the groove 240. Accordingly, the drape 244 may be held relative to the distal end 220 over the subject 20. Further piercing the drape 244 may allow for access to the divot 254 without interference of any drape or other sterile coverings such as for registration of the subject 20 and/or calibration of the instrument 16.

As discussed above, the DRF 30 will be formed of selected materials. In various embodiments the tracking portion 182, the knob 200, and the stabilization base 160 may be formed of substantially single use materials, such as entirely or substantially molded or machined polymer materials. Accordingly, the DRF 30 may be sterilized prior to the procedure and therefore need not to be covered with the drape 244 to ensure sterility of a remote incision or surgical area. Further, the DRF 30 may be sterilized for a single use and be disposed after the selected procedure.

The DRF 30, as disclosed herein, may be positioned on the subject 20 to perform a procedure, such as the one that is navigated with the navigation system 10, by the user 12. Moreover the DRF 30 may be stabilized and fixed relative to the subject 20 with substantially a single incision or only a single incision, such as the single incision 260. The single incision 260 may be sized such that additional or post procedure closures (e.g. sutures) are not needed for complete healing of the subject 20. The stabilization base 160 may be engaged to the head 20h without substantial or any trauma to the subject 20. Accordingly the DRF 30 may be used on the subject 20 during a procedure with minimal or no trauma to the subject 20 to attach the DRF 30.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for fixing a tracking device to a subject, comprising:
an anchor extending along a first axis between a first end and a second end, wherein the first end includes a base engaging portion and the second end includes a subject engaging portion that is configured to be passed through an incision in a subject and operable to engage the subject;

an elongated member extending along a second axis and having an anchor engaging portion operable to engage the base engaging portion of the anchor;

a stabilization base having a passage, wherein the elongated member is operable to pass through the passage such that the stabilization base is operable to axially move toward the anchor along the elongated member; and a knob to abut the stabilization base and axially move the stabilization base toward the subject along the elongated member;

wherein the stabilization base includes a plurality of legs, each of the legs is operable to contact the subject to three-dimensionally lock the elongated member relative to the subject;

wherein the base engaging portion is operable to pivotably engage the anchor engaging portion of the elongated member that is complementary shaped to the base engaging portion;

wherein the anchor is configured to pivot about the base engaging portion to allow the first axis of the anchor to be angled relative to the second axis of the elongated member;

wherein the anchor engaging portion includes a sidewall, wherein the sidewall defines an opening operable to allow the base engaging portion to pass and engage an internal surface of the anchor engaging portion.

2. The system of claim 1, further comprising:
a driving tool to drive the anchor into a bone of the subject.

3. The system of claim 2, wherein the anchor includes a maximum exterior dimension of about 2.3 mm.

4. The system of claim 1, wherein the elongated member includes a distal end opposite the anchor engaging portion;
wherein the distal end includes a smooth tapered outer wall and a distal portion configured to puncture a drape.

5. The system of claim 4, wherein the base engaging portion includes a spherical portion having a curved outer surface and the anchor engaging portion includes the internal surface, which is complementary shaped to the spherical portion.

6. The system of claim 5, wherein the opening is configured to allow passage of the spherical portion to enter and engage the internal surface.

7. The system of claim 1, wherein the plurality of legs includes three legs.

8. The system of claim 7, wherein each leg includes a first portion extending radially from the elongated member and a second portion that is generally parallel to an axis of the elongated member.

9. The system of claim 1, wherein each leg includes an engagement projection having a sharp penetrating distal tip.

10. The system of claim 9, wherein each engagement projection is a separate member.

11. The system of claim 1, wherein the elongated member has an external thread and the knob has an internal thread configured to threadably engage the elongated member.

12. The system of claim 1, wherein the elongated member includes a distal end opposite the anchor engaging portion;
wherein the distal end includes at least one projection extending from the distal end and configured to allow a surgical drape to be pushed over and form a small cut in the surgical drape.

13. The system of claim 12, wherein the at least one projection includes a pair of opposed projections extending from the distal end of the elongated member, each having a sharp tip.

14. The system of claim 1, wherein the elongated member includes a distal end opposite the anchor engaging portion; wherein the distal end is conically shaped.

15. The system of claim 1, wherein the base engaging portion is spaced a distance from the subject engaging portion and is configured to be spaced a distance from a bone of the subject.

16. The system of claim 15, wherein the base engaging portion and the subject engaging portion are one piece.

17. The system of claim 1, wherein the anchor engaging portion captures the base engaging portion.

* * * * *

UNITED STATES PATENT AND TRADEMARK OFFICE
CERTIFICATE OF CORRECTION

PATENT NO. : 11,090,131 B2
APPLICATION NO. : 15/957174
DATED : August 17, 2021
INVENTOR(S) : Ali Mowlai-Ashtiani It is certified that error appears in the above-identified patent and that said Letters Patent is hereby corrected as shown below:

In the Specification

Column 3, Line 61, delete "60" and insert --30-- therefor

Column 4, Line 1, delete "32," and insert --39,-- therefor

Column 6, Line 63, delete "130" and insert --132-- therefor

Column 7, Line 32, delete "200$h$." and insert --20$h$-- therefor

Column 9, Line 34, delete "174-176" and insert --174-178-- therefor

Signed and Sealed this
Fourteenth Day of June, 2022

Katherine Kelly Vidal
*Director of the United States Patent and Trademark Office*